(12) United States Patent
Phillips et al.

(10) Patent No.: US 9,192,324 B2
(45) Date of Patent: Nov. 24, 2015

(54) BREATH ALCOHOL SAMPLING SYSTEM WITH SPIROMETRIC CLIENT IDENTITY CONFIRMATION

(75) Inventors: Brian K. Phillips, Lakewood, CO (US); Geoffrey A. Wilson, Roseburg, OR (US)

(73) Assignee: International Monitoring Systems, LLC, Lakewood, CO (US)

( * ) Notice: Subject to any disclaimer, the term of this patent is extended or adjusted under 35 U.S.C. 154(b) by 541 days.

(21) Appl. No.: 13/169,603

(22) Filed: Jun. 27, 2011

(65) Prior Publication Data

US 2012/0330175 A1  Dec. 27, 2012

(51) Int. Cl.
| | |
|---|---|
| A61B 5/08 | (2006.01) |
| A61B 5/087 | (2006.01) |
| A61B 5/117 | (2006.01) |
| A61B 5/00 | (2006.01) |
| G06K 9/00 | (2006.01) |
| G07C 9/00 | (2006.01) |

(52) U.S. Cl.
CPC ............... *A61B 5/0876* (2013.01); *A61B 5/117* (2013.01); *A61B 5/4845* (2013.01); *G06K 9/00906* (2013.01); *G07C 9/00158* (2013.01)

(58) Field of Classification Search
USPC .......................................................... 600/532
See application file for complete search history.

(56) References Cited

U.S. PATENT DOCUMENTS

| | | | |
|---|---|---|---|
| 3,238,783 A | 3/1966 | Wright | |
| 3,799,149 A | 3/1974 | Rummel et al. | |
| 4,300,402 A * | 11/1981 | Dimeff | ........................ 73/861.54 |
| 4,346,584 A | 8/1982 | Boehringer | |
| 4,487,055 A | 12/1984 | Wolf | |
| 4,678,057 A | 7/1987 | Elfman et al. | |
| 4,736,619 A | 4/1988 | Legrand | |
| 4,809,810 A | 3/1989 | Elfman et al. | |
| 5,719,950 A | 2/1998 | Osten et al. | |
| 5,739,412 A | 4/1998 | Stock et al. | |
| 5,904,669 A | 5/1999 | Schildgen et al. | |
| 6,379,311 B1 | 4/2002 | Gaumond et al. | |
| 6,923,040 B2 | 8/2005 | Stock | |
| 6,967,581 B2 | 11/2005 | Karsten | |
| 6,985,070 B1 | 1/2006 | Parker | |

(Continued)

FOREIGN PATENT DOCUMENTS

| | | |
|---|---|---|
| EP | 0153741 A2 | 9/1985 |
| GB | 2121185 | * 12/1983 |

OTHER PUBLICATIONS

PCT International Search Report and Written Opinion for International Application No. PCT/US2012/032014, dated Jul. 27, 2012, 10 pages.

*Primary Examiner* — Michael Kahelin
*Assistant Examiner* — Mitchell E Alter
(74) *Attorney, Agent, or Firm* — Dorr, Carson & Birney, P.C.

(57) ABSTRACT

An system for monitoring alcohol in the breath of a test client confirms the identity of the test client based on spirometric data. The system includes a sample chamber receiving a breath sample, an alcohol sensor measuring the alcohol content of the breath sample, and a spirometric sensor generating spirometric data from the breath sample over the test client's entire exhalatory phase. A processor analyzes the spirometric data with stored client characterization data for a known client to confirm the identity of the test client. The client characterization data can be a probability density in a phase space in which at least two spirometric variables (e.g., flow and volume time-series data) are correlated.

5 Claims, 11 Drawing Sheets

(56) References Cited

U.S. PATENT DOCUMENTS

| | | |
|---|---|---|
| 6,993,378 B2 | 1/2006 | Wiederhold et al. |
| 7,329,390 B2 | 2/2008 | Stock et al. |
| 7,536,557 B2 | 5/2009 | Murakami et al. |
| 7,541,192 B2 | 6/2009 | Stock |
| 7,554,666 B2 | 6/2009 | Russell |
| 7,603,887 B2 | 10/2009 | Schlichte |
| 7,609,145 B2 | 10/2009 | Martis et al. |
| 2003/0135097 A1* | 7/2003 | Wiederhold et al. .......... 600/301 |
| 2005/0081639 A1 | 4/2005 | Gourlay |
| 2007/0177770 A1 | 8/2007 | Derchak et al. |
| 2009/0240161 A1* | 9/2009 | Sutton et al. ................. 600/538 |
| 2009/0253130 A1* | 10/2009 | Yoo ................................ 435/6 |
| 2009/0275852 A1 | 11/2009 | Oki et al. |
| 2009/0278659 A1 | 11/2009 | Barzaga Castellanos et al. |
| 2010/0108425 A1* | 5/2010 | Crespo et al. ................. 180/272 |
| 2011/0009762 A1* | 1/2011 | Eichler et al. ................. 600/532 |
| 2011/0090048 A1 | 4/2011 | Li et al. |

* cited by examiner

*Enrollment Mode*

Client Identification Confirmation

*Enrollment Mode*

*Client Identity Confirmation*

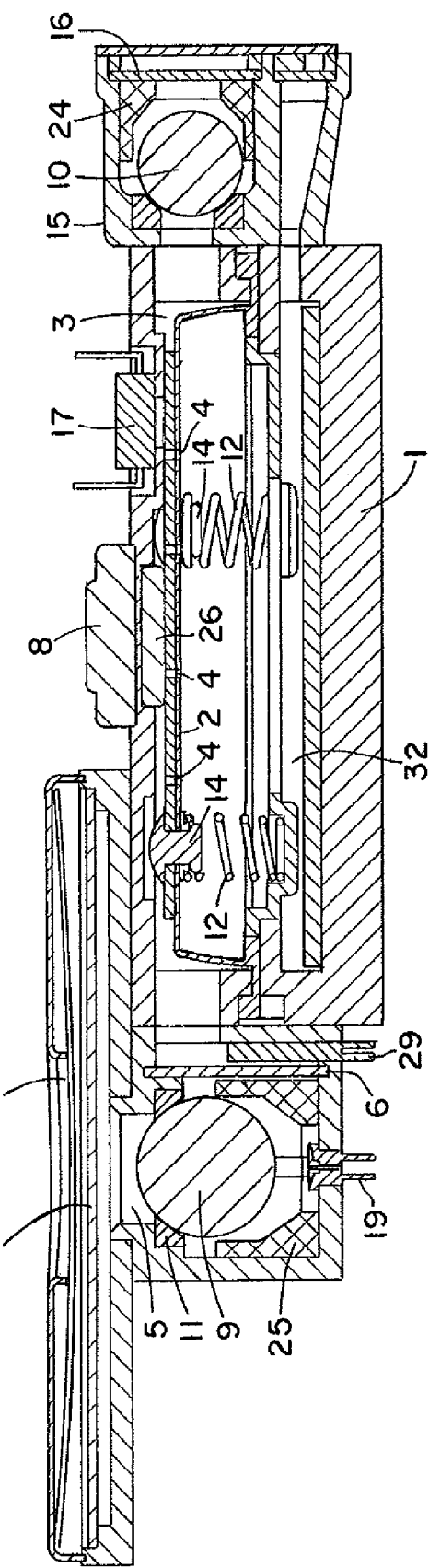
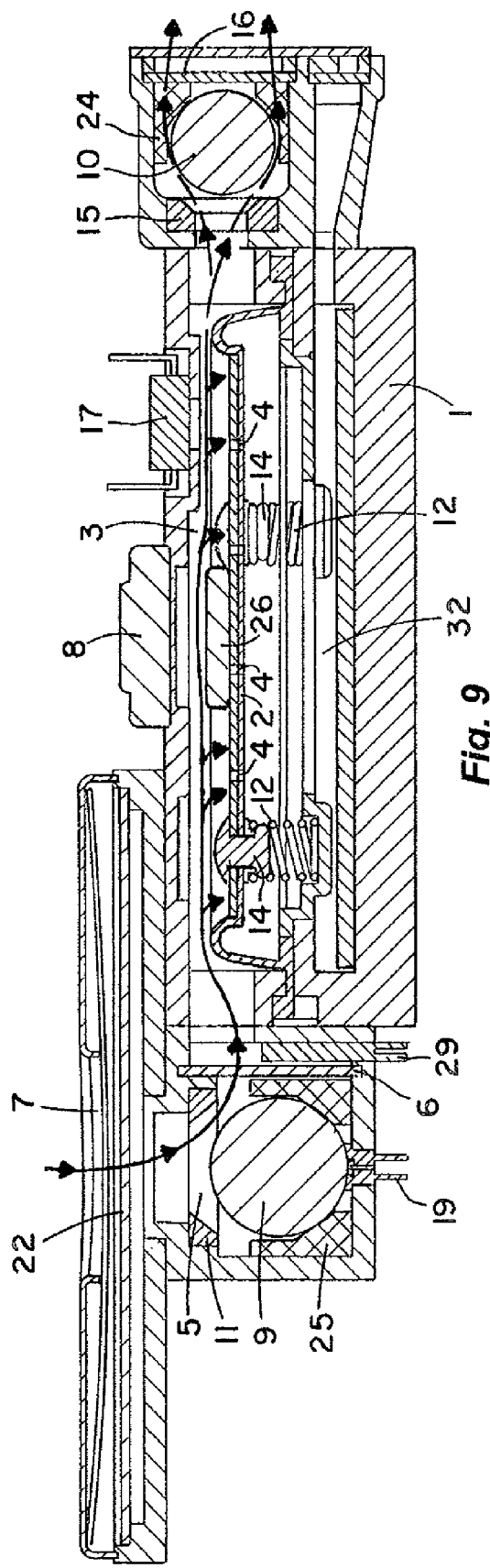

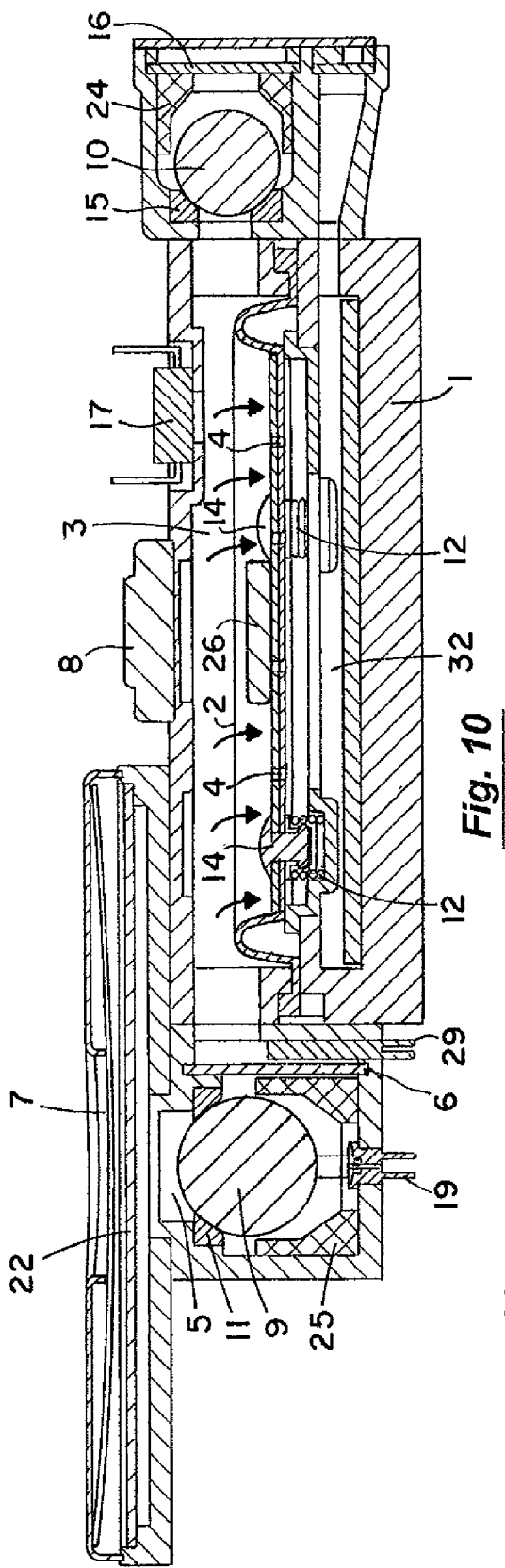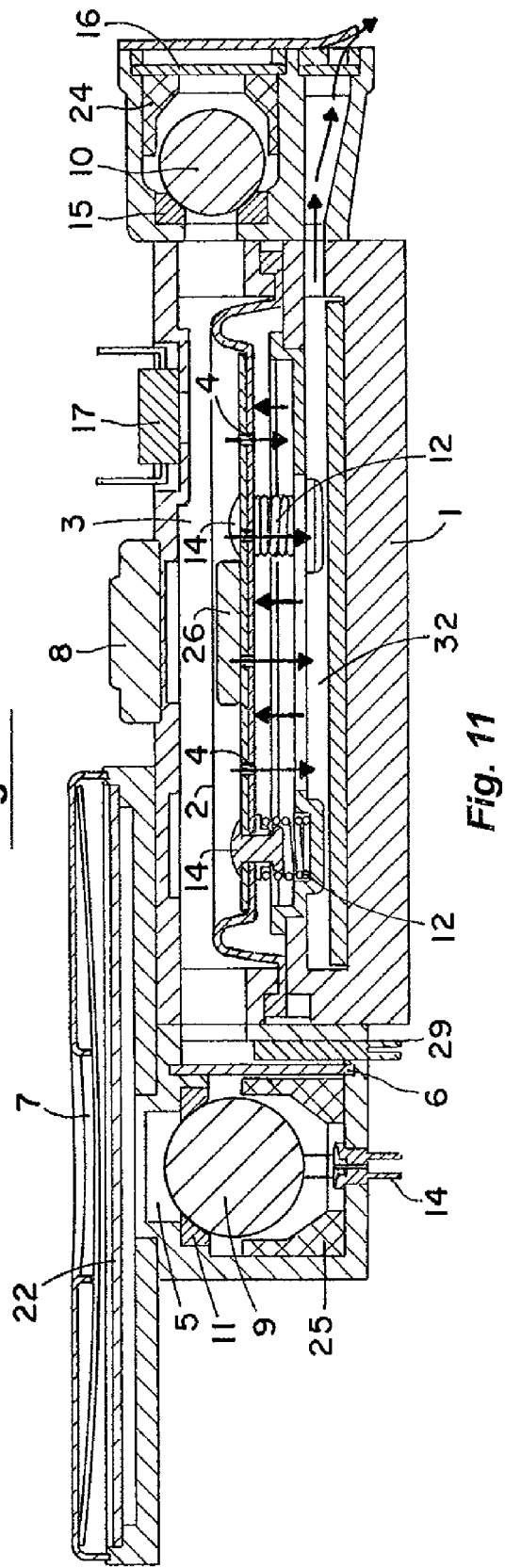

BREATH ALCOHOL SAMPLING SYSTEM WITH SPIROMETRIC CLIENT IDENTITY CONFIRMATION

BACKGROUND OF THE INVENTION

1. Field of the Invention

The present invention relates generally to the field of breath sampling devices for alcohol monitoring systems. More specifically, the present invention discloses a breath alcohol sampling system that includes spirometric client identity confirmation.

2. Background of the Invention

Biometric identification is the process of recognizing or rejecting an unknown person as a particular member of a previously characterized set, based on biological measurements. The ideal biometric characterization is specific to the individual, difficult to counterfeit, robust to metabolic fluctuations, insensitive to external conditions, easily measured, and quickly processed.

Fingerprint, retinal, iris, and facial scans are well-known biometric identification techniques relying on image processing. Images are two-dimensional, requiring sophisticated and computationally intensive algorithms, the analysis of which is often complicated by random orientation and variable scaling. Voice recognition is an example of biometric identification amenable to time series analysis, an inherently simpler one-dimensional process.

The simplest biometric identifiers can be expressed as a single parameter, such as height or weight. Single parameter identifiers have been the only quantitative means of identification throughout most of history. The price of simplicity is the loss of specificity, and in the case of weight, the lack of constancy over time. Nevertheless, single-parameter biometrics remain effective identifying factors, as is obvious from their continued use.

Client identity confirmation (CIC) is the process of periodically verifying the identity of a particular individual. More precisely, the goal is to distinguish a characterized "client" among an open-ended set of similar but uncharacterized individuals. The objective is to ensure the primary biometric measurement (e.g., breath alcohol concentration) is not falsified by the client colluding with an impostor. CIC is somewhat simpler than identification, because it merely requires distinguishing the subject from all others rather than distinguishing every individual from every other. Typically, the service period is several months, short enough to be free of the confounding effects of aging.

Spirometry is a pulmonary function testing technique for measuring airflow and lung capacity, also known as lung volume. Various spirometric parameters, along with the flow-volume loop described in the next section, are promising for CIC because they vary widely among individuals, but are fairly stable from measurement to measurement for a specific individual over a typical service period, and resist counterfeiting. It is apt to compare spirometric parameters with the familiar biometric human height—they have similar specificities (ratio of population range to individual stability) and immunities to deception.

The spirogram is a plot of lung volume versus time during a maximal inhalation and exhalation, which can diagnose airway obstructions and constrictions, inadequate diaphragm function, or thoracic cage abnormalities. FIG. 1 is a schematic spirogram of a forced vital capacity test, consisting of a maximal inhalation followed by a forced exhalation. Inhalation is depicted with a dotted line, because the invention measures only exhaled breath. This spirogram plots lung volume versus time over one cycle of maximal inhalation and forced exhalation. Spirometry is a mature clinical diagnostic, and was standardized decades ago by the American Thoracic Society (ATS).

Among the several measures of lung volume, the forced vital capacity (FVC), defined as the difference between the volumes of maximum inhalation and exhalation, and the forced expiratory volume in the first second ($FEV_1$) are particularly suit the invention. Because FVC measures the maximum air volume expellable in a single breath, it is physiologically impossible for the subject to overblow, so a measurement significantly greater than the baseline established during sensor "enrollment" indicates collusion with a cohort with more FVC than the subject. A measurement significantly lesser than the baseline indicates deception, involving either collusion with a cohort with less FVC than the subject, or the subject deliberately reserving exhalation to avoid a deep lung sample. $FEV_1$, which is rather independent of FVC, may be the most reproducible flow parameter.

The time derivative of the spirogram gives the airflow versus time. The most prominent feature of this curve is the peak expiratory flow (PEF), which is correlated to but distinct from $FEV_1$. The PEF's chief utility is that an operational shortfall relative to the enrollment baseline during operation indicates the subject is not maximally exhaling, possibly with deceptive intent.

The flow volume loop (FVL) is a plot of lung volume versus airflow, thus eliminating time as an explicit variable, while retaining implicit dynamical information. As the term "loop" implies, the FVL is cyclical or nearly so. The FVL encompasses all the spirometric parameters discussed above, therefore the shape of a client's FVL must be at least as specific as the spirometric parameter set. As the FVL may be the easiest representation of spirometric data to interpret and the most informative, it is incorporated into the example embodiment of the invention below.

FIG. 2 is a schematic FVL of a forced vital capacity test, with exhalation consisting of the positive-flow portion of the loop (solid line), proceeding counterclockwise from peak volume at time zero. The FVL plots airflow versus lung volume over one or more cycles of maximal inhalation and forced exhalation. Time has been eliminated as an explicit variable, but advances in the counterclockwise direction indicated by arrowheads. By convention, the time origin is placed at the lung capacity maximum. One can read the PEF and FVC directly from the FVL plot in FIG. 2. The exhaled volume can be found by integrating flow over time, and $FEV_1 = V(0) - V(1)$.

Diagnosis is the chief clinical application of the spirogram and related plots. Consequently, the primary aim in the medical literature is to establish norms for spirometric parameters and FVLs, according to sex, age, height, and so on. The secondary aim is sometimes to identify an ailment according to the nature of its deviation from the norm.

Furthermore, clinicians are also concerned with repeatability, to best discern borderline abnormalities and therapeutic progress. The ATS has defined repeatability as the largest and median results of three maneuvers (recorded exhalations) must differ by no more than 0.2 liters, for both FVC and $FEV_1$. Considering that a ballpark value for either parameter is two liters, the spirometry session is deemed unrepeatable if either $\Delta FVC$ is more than 10% of FVC, or $\Delta FEV_1$ is more than 10% of $FEV_1$.

Repeatability appears readily achievable. In one study of 18,000 adult patients, only 5% of the patients were unable to match their highest $FEV_1$ within 150 ml, and half matched their two largest $FEV_1$'s within 58 ml, or 3% of $FEV_1$ ("Repeatability of Spirometry in 18,000 Adult Patients", P. L. Enright et al., Am. J. Respir. Crit. Care Med. 169, pp. 235-238 (2004)). This result was irrespective of patient sex or age. Other groups have performed repeatably—a study of 852 children reported 87.9% achievement of ΔFVC less than 5% ("Forced expiratory manoeuvres in children: do they meet ATS and ERS criteria for spirometry?", H. G. M. Arets et al., Eur. Respir. J. 18, pp. 655-660 (2001)). In a study of 7,101 sufferers of chronic pulmonary obstructive disease (COPD), approximately 86% met the criterion of less than 50 mL absolute and 10% relative, for either $\Delta FEV_1$ or ΔFVC ("Variability of Spirometry in Chronic Obstructive Pulmonary Disease", L. B. Herpel et al., Am. J. Respir, Crit, Care Med. 173, pp. 1106-1113 (2006)). Other studies have reported good repeatability with children, the elderly and asthmatics.

SUMMARY OF THE INVENTION

This invention provides a breath alcohol sampling system that employs spirometric means for client identity confirmation. The system includes a sample chamber receiving a breath sample, an alcohol sensor measuring the alcohol content of the breath sample, and a spirometric sensor generating spirometric data from the breath sample. A processor analyzes the spirometric data in conjunction with stored client characterization data for a known client to confirm the identity of the test client. The client characterization data can be a probability density in a phase space in which at least two variables based on the spirometric data (e.g., flow and volume time-series data) are correlated.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which:

FIG. 8 is a cross-sectional view of a breath alcohol testing device embodying the present invention in its initial locked state.

FIG. 9 is a cross-sectional view of the breath alcohol testing device from FIG. 8 in its activated state at the beginning a breath alcohol test.

FIG. 10 is a cross-sectional view of the breath alcohol testing device from FIGS. 8-9 at the end of the breath sample.

FIG. 11 is a cross-sectional view of the breath alcohol testing device from FIGS. 8-10 illustrating gas flow from the sample chamber 3 through the small holes 4 in the diaphragm 2 into the fuel cell 1.

DETAILED DESCRIPTION OF THE INVENTION

Figure 1:
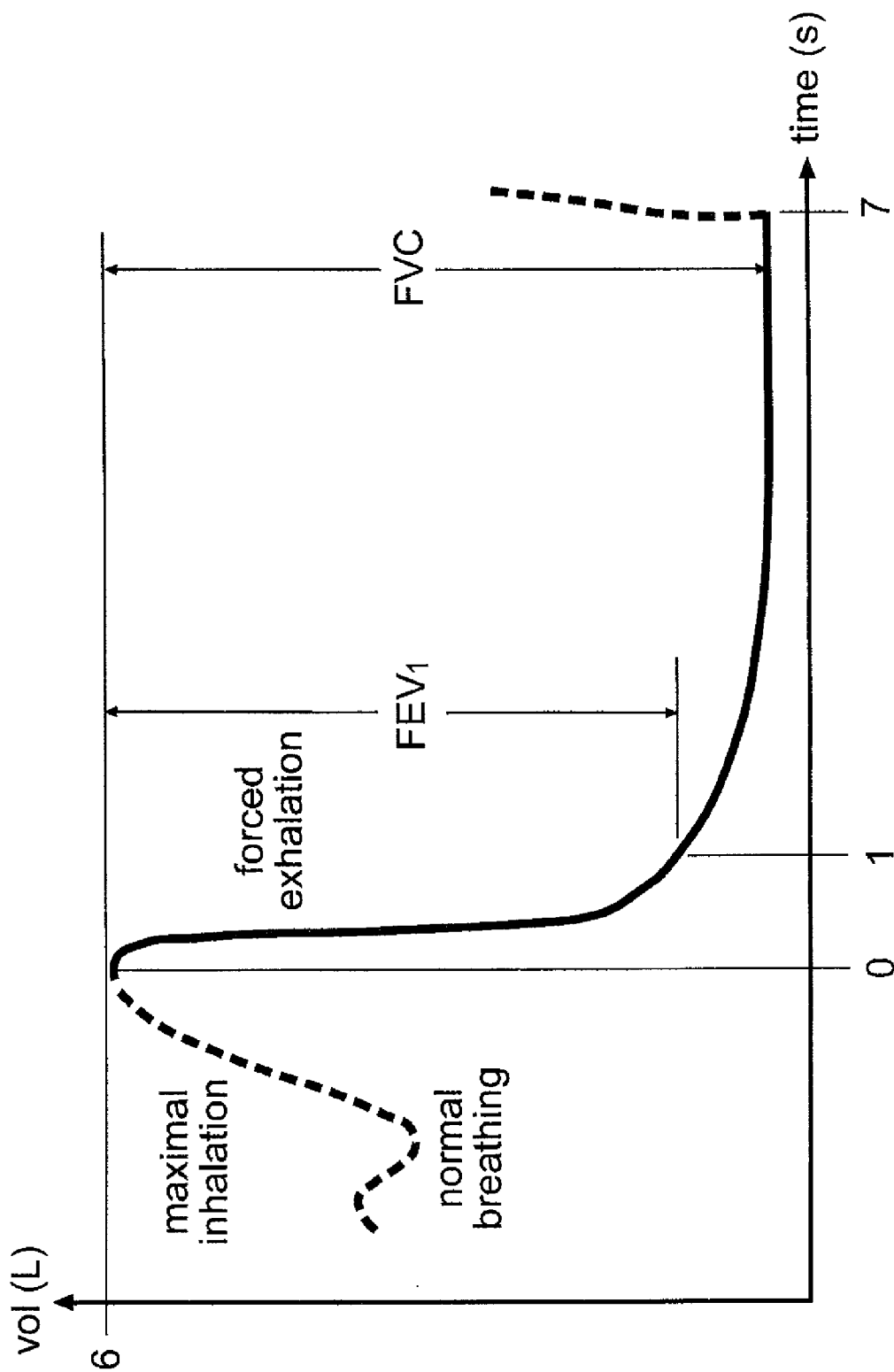
FIG. 1 is a schematic depiction of a typical spirogram resulting from forced vital capacity testing.
Figure 2:
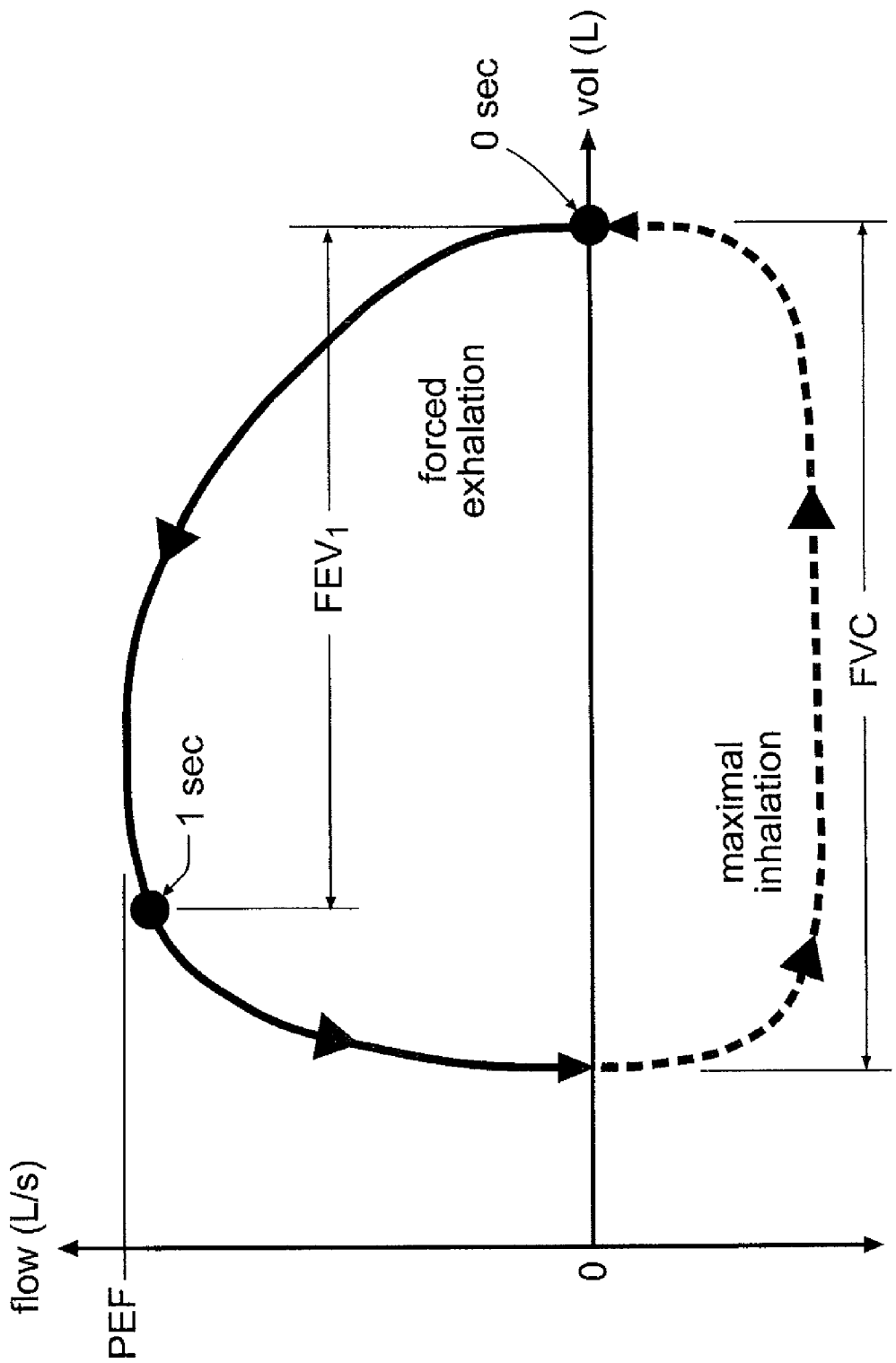
FIG. 2 is a schematic depiction of a flow-volume loop (FVL) resulting from forced vital capacity testing.
Figure 3:
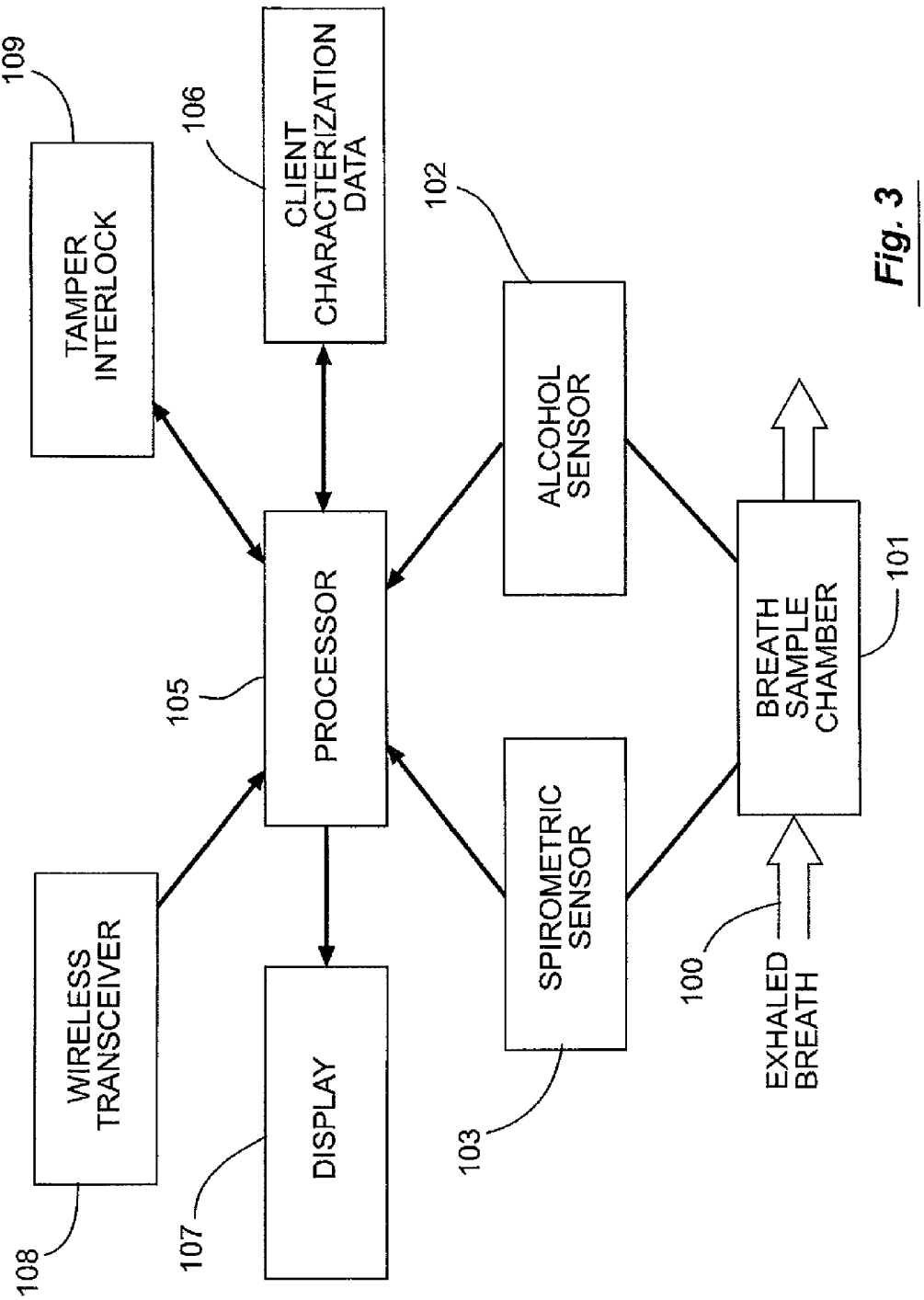
FIG. 3 is a system block diagram of the present invention.

Turning to FIG. 3, a system block diagram is provided of an embodiment of the present invention. The major components include a breath sample chamber 101 for receiving an exhaled breath sample 100 from a client. An alcohol sensor 102 detects the presence of alcohol in the breath sample, and a spirometric sensor 103 measures predetermined spirometric properties of the exhaled breath sample, such as flow or pressure. This spirometric data is typically generated as time series data over the course of the sample. For example, the alcohol sensor 102 can be an off-the-shelf alcohol monitoring component, such as an ethanol-specific electrochemical fuel cell or optical sensor that detects any alcohol present in the breath sample 100.

A computer processor 105 receives and processes data from both of these sensors 102, 103. The system can also include a conventional display 107 controlled by the processor 105, and a wireless transceiver 108 for communication with a remote center for reporting, maintenance and administration. A tamper interlock 109 detects attempts to tamper with the system or otherwise prevent it from working properly. The tamper interlock 109 can cause the processor 105 to trigger a local error/alarm indicator or report the tampering to the remote center via the wireless transceiver 108.

Optionally, the present system can also interface with a vehicle interlock system to prevent a client from operating the vehicle while intoxicated. The present system can include a location sensor (e.g., a GPS unit) in communication with the processor 105. This enables the processor 105 to determine the physical location of the unit and the subject. For example, in mobile application such as a vehicle interlock system, the processor 105 can monitor and communicate the subject's location to authorities via the wireless transceiver 108.

As an overview of operation, the present system requires an initial enrollment mode in which spirometric data for a known client is analyzed to generate client characterization data 106 identifying the known client. Thereafter, in normal operational mode, the processor 105 receives spirometric data from the spirometric sensor 103 for a test client (who may or may not be the known client). The processor 105 analyzes this spirometric data in conjunction with the client characterization data 106 to determine whether the test client is the same as the known client. For the purposes of this application, it should be understood that the phrase "test client" refers to the person whose identity is being tested or confirmed during the operational mode of the present system.

FIG. 4(a) is a flowchart of the enrollment mode employed to initially build client characterization data 106 for a known client. As FVC, $FEV_1$, and FVL are individual characteristics based on lung volume and respiratory health, the present system will include a client breath characterization process during the enrollment mode. The client will be instructed to take a deep breath and exhale completely into the sampling system. This will be completed a number of times over a period of several minutes with the resulting spirometric data being analyzed and used to generate client characterization data 106. This identifying data will be accessed during each future breath alcohol test for two purposes.

First, the client characterization data file 106 is used to confirm the client is providing a deep lung breath sample based on their capabilities. It is important to note that this feature is a significant advancement upon current breath alcohol testing devices. The current state of the art is to measure a minimum average threshold value to validate a test. With human lung capacity ranging from 1.5 to 6 liters, the opportunity for error is obvious.

Second, the client characterization data 106 is used to confirm the client is providing his own sample (i.e., to verify client identity of an in-person or a remote alcohol test). While colds and flu can create some variability, the client's lung capacity is an individual characteristic and is relatively constant over a period of months.

Figure 4:
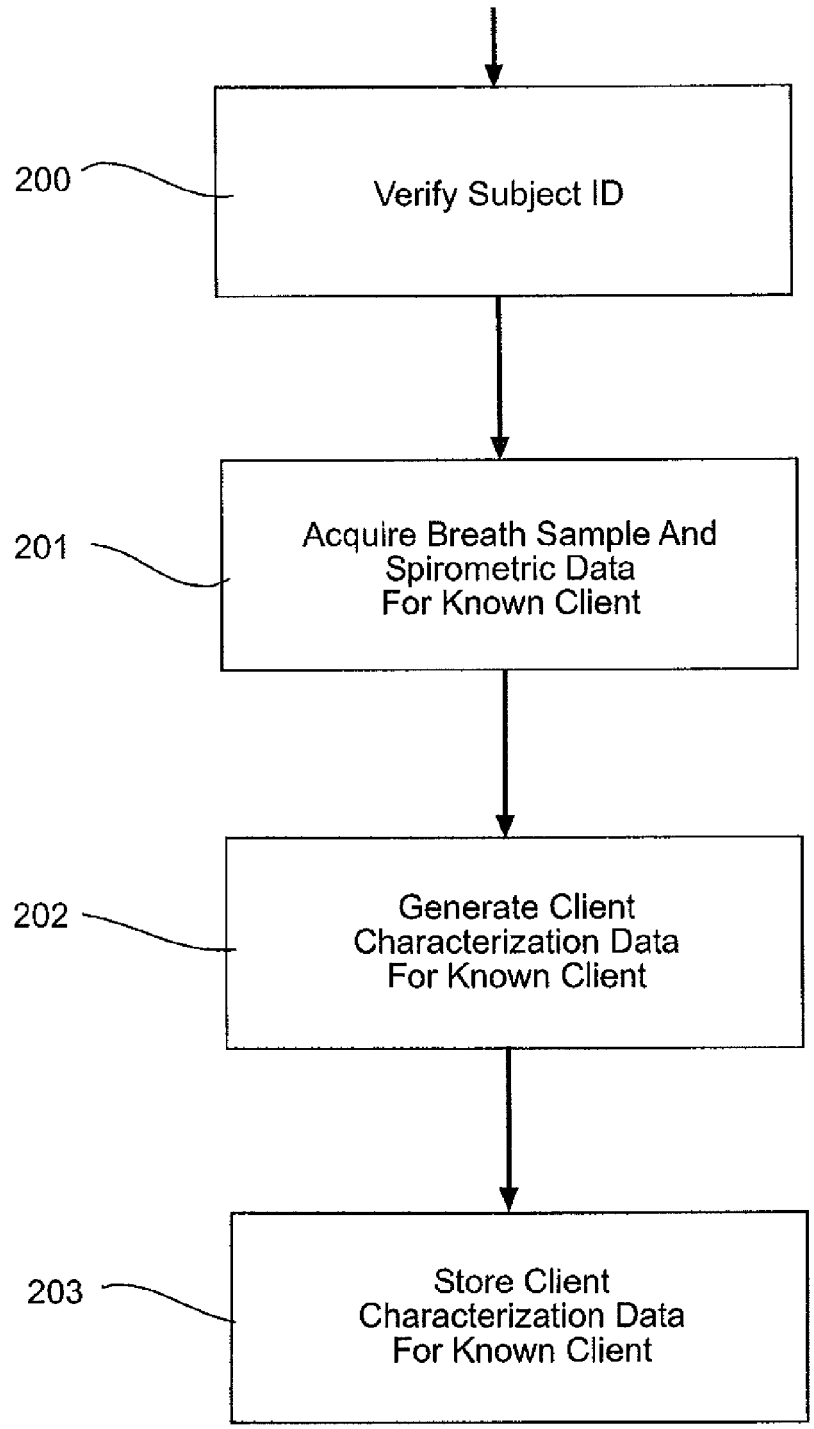
FIG. 4(a) is a flowchart of the enrollment mode of the present invention.
FIG. 4(b) is a flowchart of the client identity confirmation process as part of a typical alcohol breath test.
Figure 4:
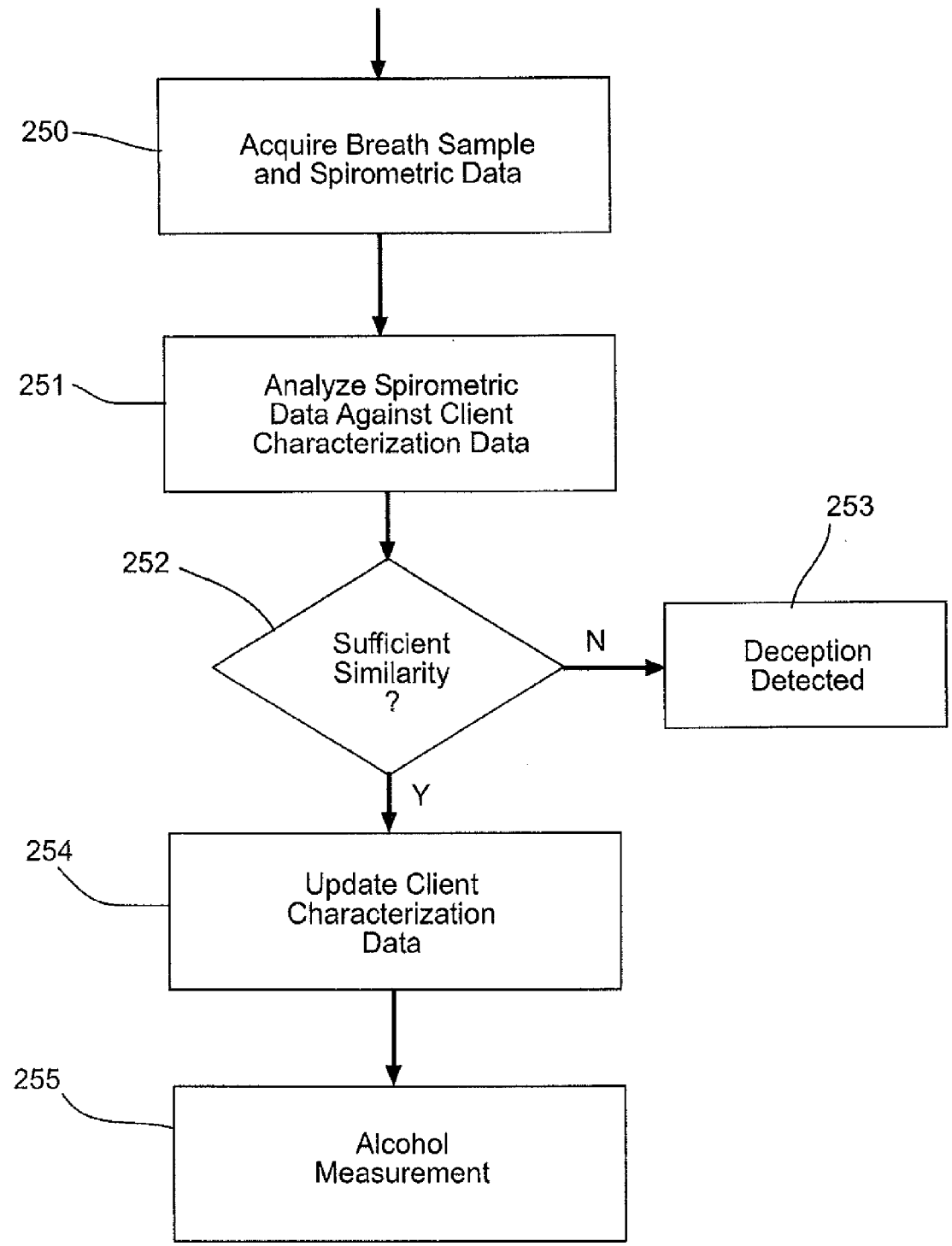

In particular, during enrollment in FIG. 4(*a*), the operator first verifies the identity of the known client (step 200). The processor 105 acquires spirometric data from the spirometric sensor 103 for a number of sample periods (step 201). The processor 105 analyzes the enrollment spirometric data and generates client characterization data 106 for identifying the known client (step 202). This client characterization data 106 is stored for later use during the operational mode of the present system (step 203) as will be described below.

Following completion of the enrollment mode, the present system proceeds to operational mode of client identity confirmation during day-to-day monitoring of the client. FIG. 4(*b*) is a flowchart of this operational mode. During each breath alcohol test, the processor 105 acquires spirometric data from the spirometric sensor 103 as the test client exhales a breath sample 100 into the breath sample chamber 101 (step 250). The processor 10 analyzes this spirometric data using the client characterization data 106 (step 251). Based on this analysis, the processor 105 determines whether there is a sufficient degree of similarity between the spirometric characteristics of the known client (from the client characterization data 106) and the test client to conclude that these are the same person (step 252). If so, the processor 105 may update the client characterization data 106 to include the current spirometric data (step 254) and then proceed with alcohol measurement in the breath sample (step 255). Otherwise, if the processor 105 determines that the current test client is not the same as the known client, an alarm can be activated to signal that deception has been detected (step 253). The processor 105 can also remotely alert the authorities via a wireless transceiver 108, or store results in a local log for later retrieval by the system administrator.

Figure 5:
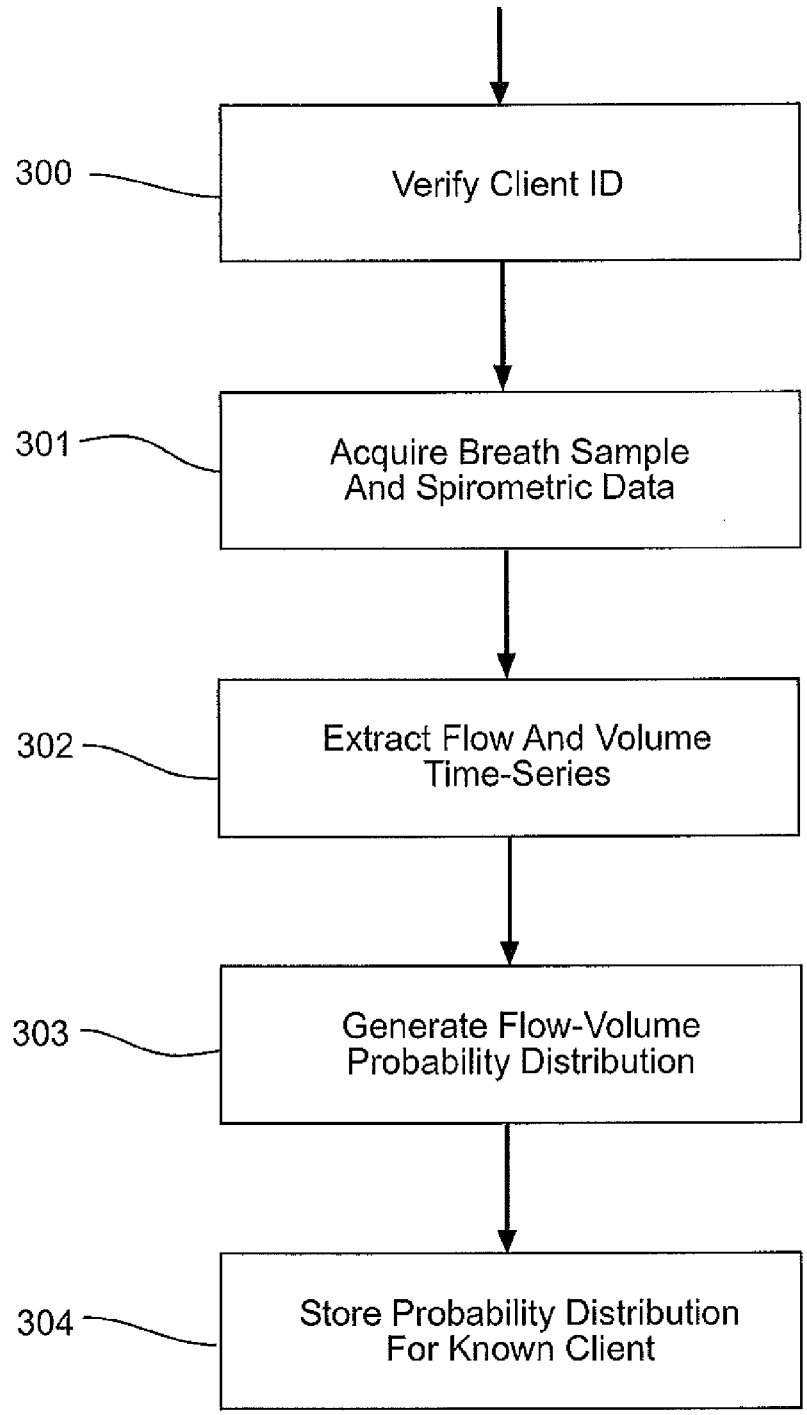
FIG. 5(a) is a flowchart of the enrollment mode for an embodiment of the present invention in which the client characterization data is stored as a probability distribution.
FIG. 5(b) is a flowchart of the process for client identity confirmation and updating the probability distribution.
Figure 5:
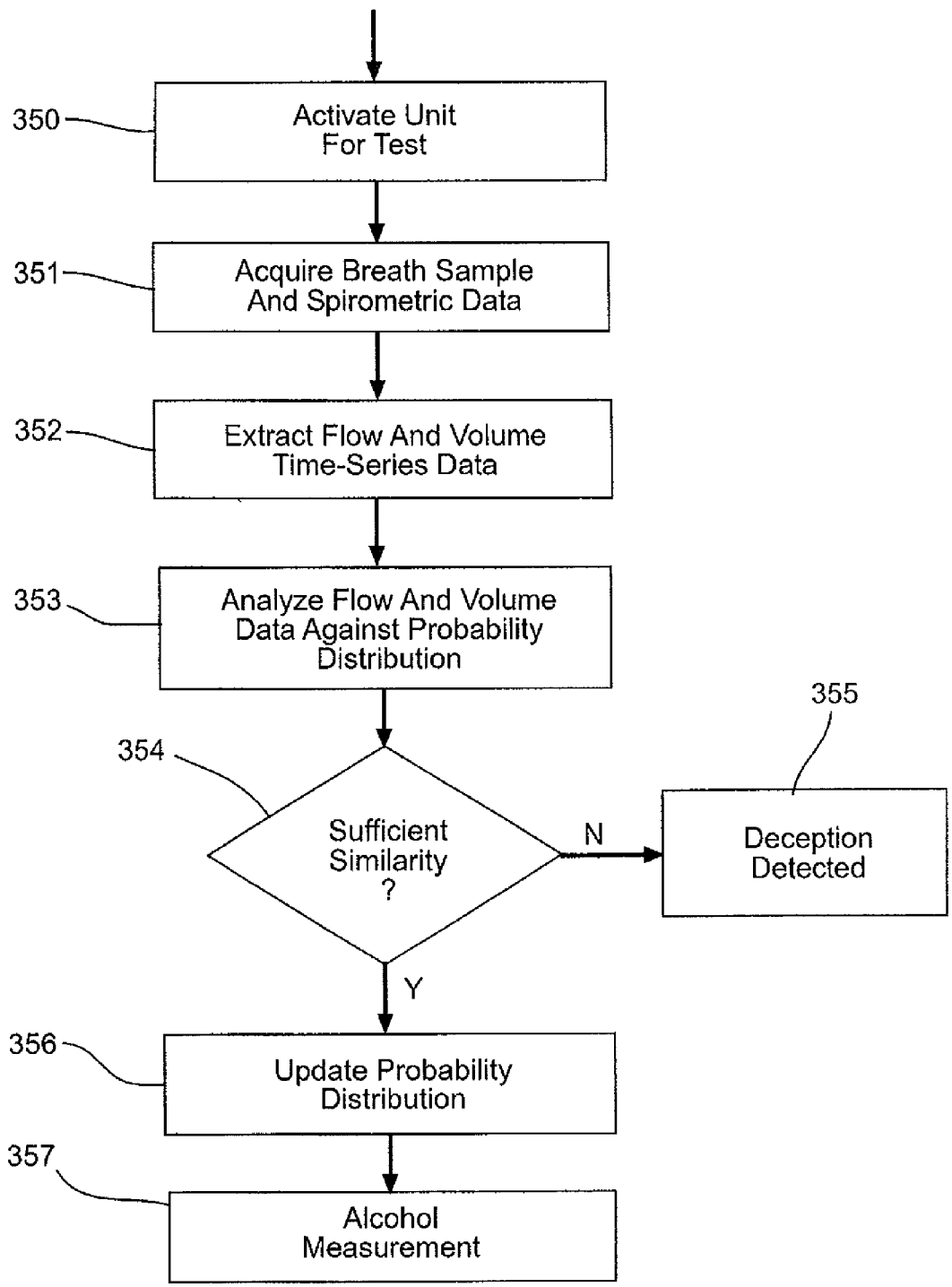

FIGS. 5(*a*) and 5(*b*) are flowcharts of the enrollment mode and operational mode, respectively, for an embodiment of the present invention in which the client characterization data 106 is stored as a probability distribution in two-dimensional phase space. As an example, the client characterization data 106 might be formulated as a learned probability density in flow-volume space. Because just exhalation is measured, only half the FVL is characterized. A strictly repeating phenomenon will trace the same sharp curve in flow-volume space over and over, while a measurement that varies from cycle to cycle will yield a blurred, probabilistic curve, as shown for example in FIG. 7. Thus, spirometric data from a number of breath samples are typically necessary to complete the enrollment process.

There are several advantages to the learned-probability approach. First, it relies on no artificial or simplistic assumptions about the dynamics, as do models. Second, it utilizes all data, rather than heavily weighting prominent features such as peak expiratory flow (PEF). Third, it naturally yields the optimal decision and probability of error in detecting identity deception.

A client's FVL probability density is acquired during the enrollment period, as generally discussed above with regard to FIGS. 4(*a*) and 4(*b*). In this embodiment, the FVL data from multiple breath samples for the client are combined and stored as a probability distribution in phase space. This probability distribution serves as the client characterization data 106, discussed above.

In general terms a "phase space" is a multi-dimensional (D dimensional) space in which a spirometric variable is correlated with (D−1) other measurements. The other measurements can be the same variable measured at various times in the past, or other contemporary variables, or a combination. The D measurements form a vector that traces an "orbit" or repeating pattern in phase space over a series of breath samples. A strictly periodic phenomenon will follow the same orbit over and over, and will soon be utterly predictable. A phenomenon that varies from breath sample to sample will yield a blurred, probabilistic orbit.

Figure 6:
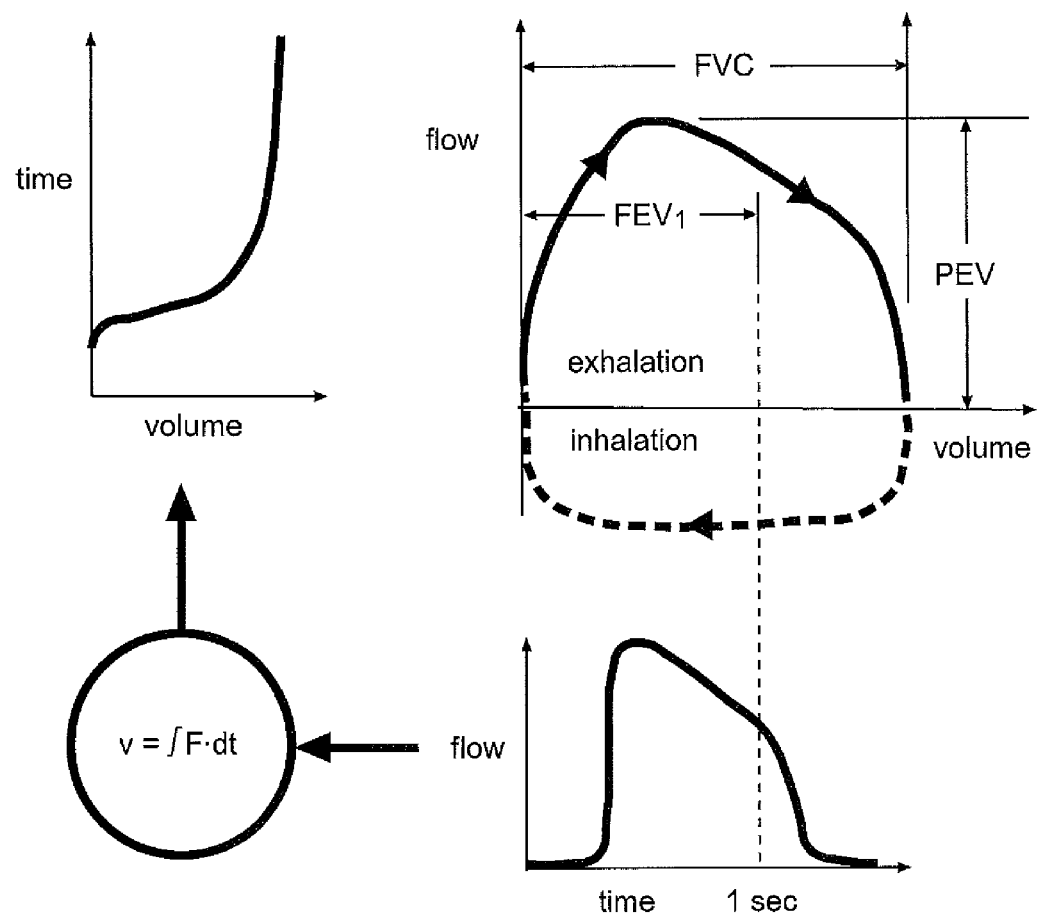
FIG. 6 depicts graphs illustrating how spirometric flow time-series data can be integrated over time to generate volume time-series data. The flow data and volume data can then be combined to generate a FVL.
Figure 7:
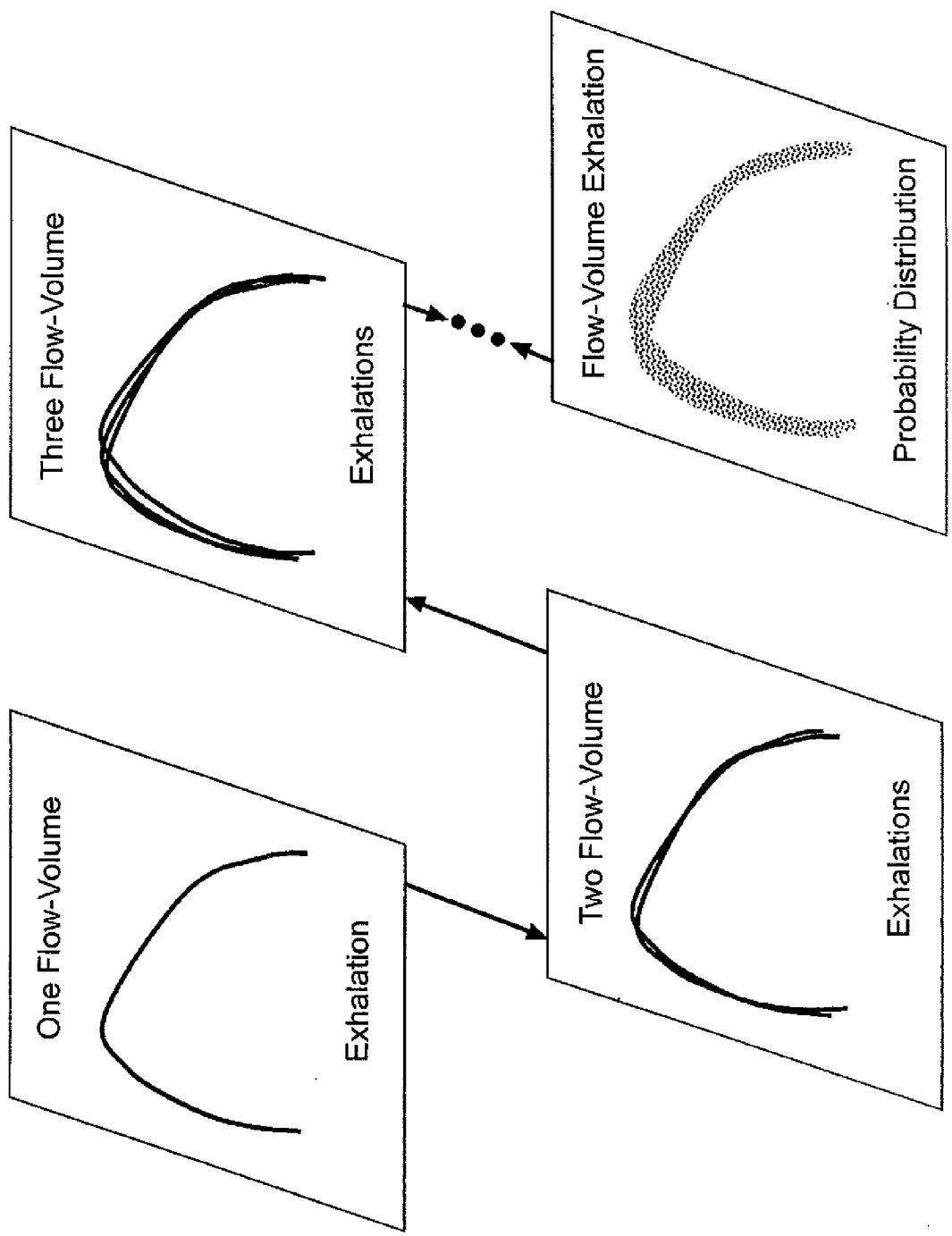
FIG. 7 is a diagram illustrating the manner in which a probability distribution can be built up from spirometric data over many respiratory cycles.

This specific embodiment employs flow and volume time-series data as the variables in the probability distribution. FIG. 6 depicts the reduction of flow and volume time-series into a flow versus volume orbit in phase space. FIG. 7 is a diagram illustrating how a flow-volume probability distribution can be built up over many breath samples.

The phase space domain is usually just the outer product of its scalar variable domains. With 8-bit analog-to-digital conversion (ADC), a 2-D phase space needs but a modest 65,536-address memory. An 8-bit ADC is probably adequate, considering the small dynamic range and noisiness of the signals. The phase space range should be appropriate for storing a probability—for instance, an unsigned integer. Since the orbit visits some phase space cells much more frequently than others, the integer must have sufficient dynamic range, say 16 bits. Thus, the example phase space probability density memory requirement is 128 kilobytes. In other words, the phase space is effectively a 2-D array of cells or elements, each of which store an integer value representing the probability associated with a particular pair of flow and volume values for the client. This phase space can be referred to as a flow-volume probability distribution.

Returning to the enrollment mode in FIG. 5(*a*), the identity of a known client is first verified in step 300. This client is then required to blow into the sensor a number of times in the presence of a technician so that several sets of spirometric data can be acquired (step 301). The spirometric data is then analyzed to extract flow and volume time-series data (step 302). The flow data and volume data can then be combined to generate a FVL (step 303), which is stored as a probability distribution (step 304) for later use in the operational mode.

After enrollment, the system can be used in its operational mode. FIG. 5(*b*) is a flowchart of the operational mode for this embodiment. Prior to each breath test, the unit is first activated by the client (step 350). For example, this can be done by activating a switch, or by sensing contact with the client's lips, or by pressure exerted by the client's exhalation into the unit. During the breath sample, the processor 105 acquires spirometric time-series data from the spirometric sensor 103 for the test client (step 351). The processor 105 converts this raw data into flow and volume time-series data (step 352). The flow-volume probability distribution serves as a look-up table for the probability associated with each pair of flow and volume values measured during operational mode. In particular, the processor 105 retrieves from the flow-volume probability distribution the probability associated with the pairs of flow and volume values. Analysis of the probabilities associated with the set of pairs of flow and volume values enables the processor 105 to determine whether there is a sufficient similarity between the spirometric characteristics of the known client and test client currently using the unit (step 353).

The probability density can be quite specific to a client, without assuming any particular model. Deception is detected when the compound probability of measuring the latest N data is deemed sufficiently small (step 354). More specifically, a deception is judged when the cost of erroneously regarding the subject as truthful exceeds the cost of erroneously regarding the subject as deceptive: $C(t|D) \times P(D|M) > C(d|T) \times P(T|M)$, where $C(t|D)$ is the penalty for judging the subject truthful when in fact deceptive, and $P(D|M)$ is the (unknown) conditional probability of deception given the measurement M, and vice versa for the right-hand side of the inequality.

Bayes' Theorem states: $P(D|M) \times P(M) = P(D,M) = P(M|D) \times P(D)$, where $P(M)$ is the (inconsequential) a priori probability of measuring M, $P(D,M)$ is the (undesired) joint probability of deception and measuring M, $P(M|D)$ is the (known) conditional probability of measuring M given deception, and $P(D)$ is the (estimated) probability of deception. Substituting into the cost condition and rearranging gives $P(M|D)/P(M|T) \times P(D)/P(T) > C(d|T)/C(t|D)$. These factors are all known or estimated: $P(M|D)$ is given by the average of all subjects' probability densities, assuming this average represents the general population, and the subject is as likely to pass off the sensor to anyone as to anyone else; $P(M|T)$ is given by the subject's own probability density; $P(D)$ is estimated from a subject's past behavior (e.g., a subject who has not attempted deception in three tests per day for a month has on the order of 1% chance of attempting deception on the next test); $P(T)$ is merely $1 - P(D)$; and $C(d|T)$ and $C(t|D)$ are input parameters.

The specificity of client identity confirmation can be quantified by the probability of the client successfully colluding with a random impostor. As previously noted, the FVL (encompassing the FVC, $FEV_1$, PEF and possibly other spirometric parameters) must be at least as specific as the parameter vector (FVC, $FEV_1$, PEF, ...). Thus, the specificity estimated for the parameter vector is pessimistic, and the actual FVL specificity may be better. For most of the population, FVC and $FEV_1$ each span approximately a factor of two. Since repeatability is typically about 5%, a random member of the population can be assigned to one of about ten classes for each of FVC and FEW PEF is strongly correlated with $FEV_1$, but since it's a peak rather than an integrated measure, it's likely noisier. Therefore, PEF is not considered in this analysis.

Suppose FVC and $FEV_1$ each span ten distinguishable classes. Using either by itself yields a 10% probability of successful deception. Were FVC and $FEV_1$ fully independent, and matching both were required, the probability of successful deception drops to 1%. If FVC and $FEV_1$ were perfectly correlated, checking either is as good as checking both, and the probability of successful deception remains about 10%. The geometric mean, about 3% is a realistic expectation. Thus, the combination of FVC and $FEV_1$ for client identity confirmation will false-negative (report all is well, when in fact an impostor has supplied the breath sample) about one time in thirty.

Since performance is limited from above by mechanical and physiological constraints, breath tests resulting in the largest FVLs are most trustworthy. The greatest or greatest few measurements initialize the probability density. Enrollment serves the concomitant function of training the subject to put forth a maximal effort. After enrollment, and during normal operation, new data deemed genuine updates the probability density (step 356). In order to weight new data more than old data, and to prevent overflow, the accumulated probability density is continuously devalued. On the other hand, if data is deemed bogus, the system can alert the authorities to possible deception (step 355). Bogus data should obviously not be allowed to corrupt the probability density for the subject. Assuming the identity of the test client is validated, the system can proceed with measurement of any alcohol in the breath sample (step 357).

Another embodiment of the present invention relies on statistical analysis of a plurality of spirometric parameters for each client. In other words, the client characterization data includes a plurality of spirometric parameters, such as FVC, PEF and $FEV_1$. Data from a statistically significant set of breath samples can be acquired and analyzed during the initial enrollment period and also during the subsequent operational mode to determine mean and standard deviation values for each of these spirometric parameters. The use of a combination of multiple spirometric parameters increases the confidence of a correct identification of a client.

In yet another embodiment of the present invention, the shape of the flow curve during the expiratory phase can be characterized by a number parameters. In particular, a typical flow versus time curve is generally trapezoidal consisting of the following stages. First, there is a rapid onset with flow increasing over a few tenths of a second from zero to PEF at the beginning of exhalation. Next, there is a gradual diminution in flow over several seconds during exhalation, which can be characterized by a slope, dF/dt, and possibly a curvature parameter. Finally, there is a rapid decrease in flow to zero (or "collapse"), when no more air is exhaled.

For example, this type of analysis can yield the following parameters: (1) PEF—technically, the largest flow value in the data set, but a more repeatable proxy for $F_{max}$, the intercept of a linear least-squares fit to the droop-stage data; (2) dF/dt—the slope of the least-squares fit to the droop-stage data; and (3) FVC—the time integral of flow over all three stages. Other possible sets of spirometric parameters include $V_{max}$, $F_{max}$ and dF/dt. Here again, means and standard deviation values can be calculated and stored for each of these spirometric parameters.

In some cases, the use of a trapezoidal paradigm may be too simplistic. Some breath profiles show a substantial roundedness and are better modeled by quadratic or polynomial curve fitting. In this embodiment, the resulting coefficients from quadratic or polynomial curve fitting, together with FVC, could serve as the spirometric parameters.

The breath sampling system depicted in the cross-sectional views provided in FIGS. 8-11 illustrates one possible physical embodiment of the present invention. This system offers several key advancements and innovations in the field of breath alcohol testing. First, the system has only passive mechanical components, without electrically-powered pumps or valves. Sampling is powered solely by the mechanical energy of exhalation. The system has only four moving parts, thereby providing excellent mechanical reliability. In contrast, many conventional breath sampling devices employ a mechanical pump, which increase power requirements and are often prone to failure.

Second, the present system ensures a deep lung breath sample is transferred to the breath alcohol concentration sensor to avoid spuriously low or high readings. Third, the present system provides spirometric client identity confirmation (CIC). Finally, the only active components are a temperature sensor for breath temperature compensation, an infrared proximity sensor/diaphragm for measuring airflow, and an interrupt mechanism for detecting the commencement and cessation of exhalation. It should be understood that other types of pressure or flow sensors may be substituted for the diaphragm deflection/proximity sensor arrangement. The present system can be is enclosed in a compact housing.

In this embodiment of the present invention, the sampling procedure and the breath alcohol concentration analyzer hardware dovetail together well. An accurate breath alcohol measurement requires an air sample from deep within the lungs, essentially the tail end of a maximal exhalation. The usual strategies for subverting a breath alcohol test—reserving exhalation and counterfeiting the sample—are precisely those the present invention is designed to foil.

FIG. 8 is a cross-sectional view of the breath alcohol testing device in its initial locked state (i.e., prior to a breath test). A magnetic coil 8 on the housing of the unit attracts a small permanent magnet 26 attached to the diaphragm 2, so that the diaphragm 2 is held in place against the interior of the unit housing to prevent damage during transportation or storage of the unit, and to assure a uniform starting position of the diaphragm.

FIG. 9 is a cross-sectional view of the breath alcohol testing device in its activated state at the beginning a breath alcohol test. The magnetic coil 8 releases the magnet 26 to allow the diaphragm 2 to move during the testing process. In operation, the subject presses his lips against the lip contact plate 7, and blows into the entry chamber 5. The breath traverses a porous hydrophobic membrane 22, and its positive pressure dislodges the metal ball valves 9 and 10 from their respective magnetic washers 11 and 15 into ball valve cages 25 and 24, as shown in FIG. 9. This allows the breath gases to flow from the inlet ball valve 9 through a secondary membrane 6 into an upper sample chamber 3, and then exit at the outlet ball valve 10 through an exhaust membrane 16.

The pressure generated by blowing separates the inlet ball valve 9 from its magnetic washer 11 and makes contact with activation contacts 19 This closes a low-power circuit causing an interrupt to awake a processor and inform it that a breath alcohol test is taking place. The processor then reads a baseline from the breath alcohol concentration sensor (fuel cell 1) and reads the temperature of the breath via a temperature sensor 29. The processor also reads the deflection of the diaphragm 2 via an infrared sensor 17 to assure it is depressed by positive pressure, and initiates a counter.

The flow restriction provided by the outlet ball valve 10 serves as a known resistance, which creates back pressure within the upper sample chamber 3. As this pressure builds, the diaphragm 2 is depressed toward the base of the fuel cell sample chamber 32, as shown in FIG. 10. Repeatable resistance to this downward movement of the diaphragm 2 is provided by a number of compression springs 12. Any air in the fuel cell sample chamber 32 is purged through the exhaust port 21 as the diaphragm 2 is incrementally depressed. During exhalation, an infrared sensor 17 measures the diaphragm 2 deflection at predetermined intervals. Due to the known resistance of the outlet ball valve 10, changes in the position of the diaphragm are proportional to changes in pressure within the sample chamber. The processor 105 can then calculate total breath flow based on diaphragm deflection versus time over the sampling period.

Temperature readings can be utilized to calibrate both the spirometric measurements and the reported breath alcohol concentration; and to confirm the sample is in the 30° C. to 37° C. range expected of a human test subject, as part of client identity confirmation. The counter will time the duration of flow through the fuel cell sample chamber 32, starting with the interrupt generated by breaking interrupt contacts 19, and stopping when exhalation finishes, remaking contact. This informs the microprocessor that breath sampling has ended, and the deep lung breath alcohol sample is now in the external sample chamber.

Upon the reduction in pressure as exhalation ends, the metal ball valves 9 and 10 are attracted to the magnetic washers 11 and 15, returning to their original closed and sealed position, as shown in FIG. 11. Compression springs 12 mounted to rivets 14 under the diaphragm 2, having been compressed by the back pressure of exhalation on the flow restriction provided by the outlet ball valve 10, gradually move the diaphragm 2 upward to its quiescent position. As this occurs, the breath in the upper sample chamber 3 is forced through a number of small-diameter holes 4 or reed valves in the face of diaphragm 2. The small-diameter holes 4 allow a calibrated breath sample to enter the fuel cell's internal sample chamber 32.

The breath sample is presented to the breath alcohol concentration sensor (e.g., a fuel cell 1 that oxidizes ethanol and converts it to a proportional electrical signal). Any ethanol measurement sensor may be substituted, particularly infrared measurement systems. The processor 105 then computes the breath alcohol concentration using the fuel cell output, breath sample temperature, fuel cell temperature, and various calibration factors.

The present invention could also employ a mechanical flow meter piggybacking on an existing breath alcohol sampler hardware design, providing an exhaled air-flow time series to the processor 105. Alternatively, air flow can be inferred from the pressure drop across a calibrated orifice. The air flow may be time-integrated to yield the FVC, thus also providing the spirogram and FVL.

The above disclosure sets forth a number of embodiments of the present invention described in detail with respect to the accompanying drawings. Those skilled in this art will appreciate that various changes, modifications, other structural arrangements, and other embodiments could be practiced under the teachings of the present invention without departing from the scope of this invention as set forth in the following claims.

We claim:

1. An apparatus for monitoring alcohol in the breath of a test client, said apparatus comprising:
   a sample chamber receiving a breath sample during the exhalatory phase of a test client;
   an alcohol sensor measuring the alcohol content of the breath sample from the sample chamber;
   a spirometric sensor generating spirometric data over a test clients entire exhalatory phase from the same breath sample into the sample chamber;
   a means for storing client characterization data based at least in part on the shape of the flow versus time curve of the exhalatory phase for a known client, wherein the client characterization data comprises a probability density in a phase space in which a first spirometric variable is correlated with at least a second spirometric variable; and
   a processor analyzing spirometric data from the spirometric sensor and stored client characterization data to determine whether the test client is the known client.

2. The apparatus of claim 1 wherein the probability density is generated from flow time-series data correlated with volume time-series data.

3. An apparatus for monitoring alcohol in the breath of a test client, said apparatus comprising:
   a sample chamber receiving a breath sample from a test client, said sample chamber having:

(a) a diaphragm;
(b) an inlet valve; and
(c) an outlet valve having a flow resistance creating back pressure within the sample chamber in response to the breath sample, thereby resulting in movement of the diaphragm during the breath sample; said inlet and outlet valves closing at the end of the breath sample to contain the breath sample within the sample chamber;

an alcohol sensor measuring the alcohol content of the breath sample in the sample chamber;

a spirometric sensor generating spirometric data by measuring movement of the diaphragm during the same breath sample;

a means for storing client characterization data based at least in part on the shape of the flow versus time curve of the exhalatory phase for a known client, wherein the client characterization data comprises a probability density in a phase space in which a first spirometric variable is correlated with at least a second spirometric variable; and a processor analyzing spirometric data from the spirometric sensor and stored client characterization data to determine whether the test client is the known client.

4. The apparatus of claim 3 wherein the probability density is generated from flow time-series data correlated with volume time-series data.

5. The apparatus of claim 3 wherein the probability density is initially generated from spirometric data acquired during an enrollment mode, and then updated with spirometric data acquired during subsequent breath alcohol tests for the test client.

\* \* \* \* \*